(12) United States Patent
Subedi

(10) Patent No.: US 10,285,671 B2
(45) Date of Patent: May 14, 2019

(54) SYSTEM, METHOD AND APPARATUS FOR INTEGRATED TISSUE SAMPLING AND TISSUE MARKER PLACEMENT

(71) Applicant: Device and Design, LLC, Austin, TX (US)

(72) Inventor: Shree K. Subedi, Austin, TX (US)

(73) Assignee: Device and Design, LLC, Austin, TX (US)

( * ) Notice: Subject to any disclaimer, the term of this patent is extended or adjusted under 35 U.S.C. 154(b) by 0 days.

(21) Appl. No.: 15/888,527

(22) Filed: Feb. 5, 2018

(65) Prior Publication Data
US 2018/0221001 A1 Aug. 9, 2018

Related U.S. Application Data

(60) Provisional application No. 62/454,955, filed on Feb. 6, 2017.

(51) Int. Cl.
*A61B 10/02* (2006.01)
*A61B 90/00* (2016.01)

(52) U.S. Cl.
CPC ...... *A61B 10/0233* (2013.01); *A61B 10/0275* (2013.01); *A61B 10/0283* (2013.01);
(Continued)

(58) Field of Classification Search
CPC ............ A61B 10/0233; A61B 10/0266; A61B 10/0283; A61B 90/39; A61B 2090/3904; A61B 2090/3908; A61B 2090/3987
See application file for complete search history.

(56) References Cited

U.S. PATENT DOCUMENTS

| 5,782,775 A | 7/1998 | Milliman et al. |
| 6,432,064 B1 * | 8/2002 | Hibner ............... A61B 10/0275 |
| | | 128/897 |

(Continued)

FOREIGN PATENT DOCUMENTS

| JP | 5102207 B2 | 12/2012 |
| WO | 2007021904 A2 | 2/2007 |

OTHER PUBLICATIONS

Communication from a foreign patent office in a counterpart foreign application, ISA/US, International Search Report and Written Opinion of the International Searching Authority for International Application No. PCT/US2018/016888, dated Apr. 23, 2018, 12 pages.

*Primary Examiner* — Devin B Henson
(74) *Attorney, Agent, or Firm* — Patterson Thuente Pedersen, P.A.

(57) ABSTRACT

A medical device can include an actuator that is gripped and manipulated by an operator of the medical device. An outer cannula can extend from the actuator along an axis. The outer cannula can include a tissue reception port. An inner cannula can be located inside the outer cannula and extend in an axial direction. An inner lumen can be located inside the inner cannula and actuated to collect a tissue sample via the tissue reception port. In addition, a secondary lumen can be adjacent to the outer cannula and actuated to deploy a marker at a biopsy site via a marker deployment port. Tissue sampling and marker placement functions can be integrated within only one medical device such that the medical device is a single apparatus that performs both tissue sampling and marker placement functions.

19 Claims, 4 Drawing Sheets

(52) U.S. Cl.
 CPC ...... *A61B 90/39* (2016.02); *A61B 2090/3908* (2016.02); *A61B 2090/3987* (2016.02)

(56) References Cited

U.S. PATENT DOCUMENTS

| | | | |
|---|---|---|---|
| 7,001,341 B2 * | 2/2006 | Gellman | A61B 10/0275 600/562 |
| 7,465,279 B2 | 12/2008 | Beckman et al. | |
| 8,052,708 B2 | 11/2011 | Chesbrough et al. | |
| 8,167,817 B2 * | 5/2012 | Vetter | A61B 10/0266 600/562 |
| 8,282,574 B2 | 10/2012 | Coonahan et al. | |
| 8,454,629 B2 | 6/2013 | Selis | |
| 2009/0076412 A1 * | 3/2009 | Rioux | A61B 10/0266 600/564 |
| 2009/0076521 A1 * | 3/2009 | Hansen | A61B 17/3468 606/129 |
| 2009/0227893 A1 | 9/2009 | Coonahan et al. | |
| 2010/0113920 A1 | 5/2010 | Foerster et al. | |
| 2012/0184874 A1 | 7/2012 | Vetter et al. | |
| 2012/0302913 A1 | 11/2012 | Miller | |
| 2012/0323120 A1 | 12/2012 | Taylor et al. | |

\* cited by examiner

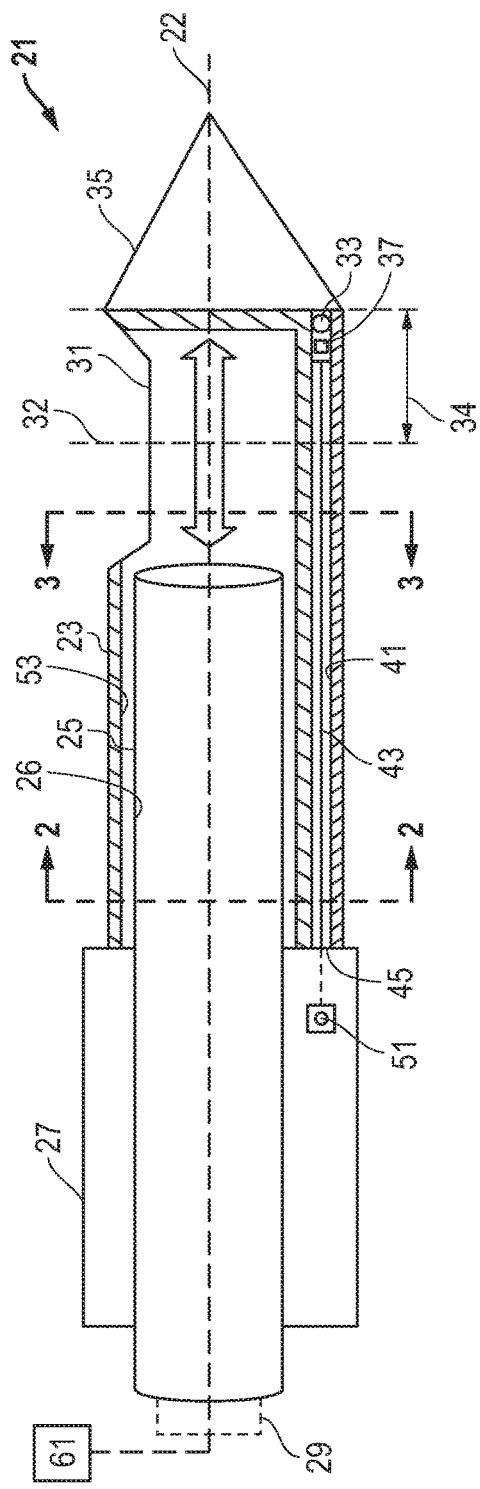
FIG. 1
FIG. 2
FIG. 3

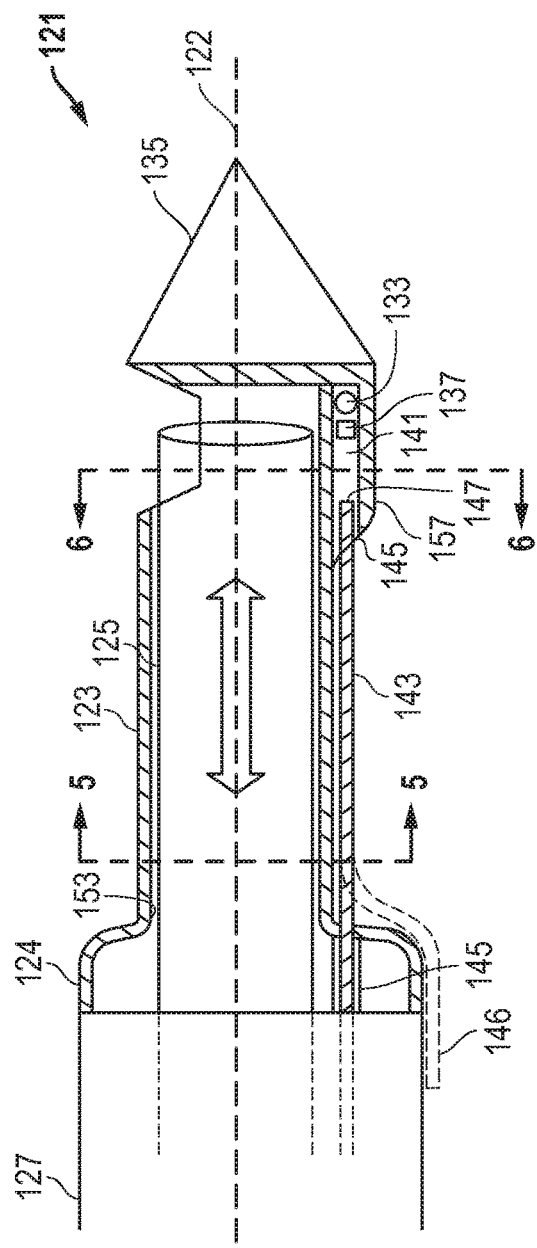
FIG. 4
FIG. 5
FIG. 6

SYSTEM, METHOD AND APPARATUS FOR INTEGRATED TISSUE SAMPLING AND TISSUE MARKER PLACEMENT

This application claims priority to and the benefit of U.S. Prov. Pat. App. No. 62/454,955, filed Feb. 6, 2017, which is incorporated herein by reference in its entirety.

BACKGROUND OF THE INVENTION

Field of the Disclosure

The present invention relates in general to medical devices and, in particular, to a system, method and apparatus for integrated tissue sampling and tissue marker placement.

Description of the Prior Art

Breast cancer is the second most common cause of cancer deaths in the United States. Early detection and treatment of breast cancer is important to decrease cancer related mortality and to improve disease-free survival. Various imaging modalities (e.g. mammography, tomosynthesis, ultrasound, MRI) are used in screening, diagnosis and treatment of breast cancer. If cancer is suspected based on clinical exam and/or imaging findings, further evaluation is commonly done with percutaneous biopsy to obtain tissue samples which are subsequently sent for laboratory analysis. More than 1.5 million breast biopsies are estimated to be performed in the United States every year, and more than 5 million breast biopsies are estimated to be performed in the rest of the world every year.

Currently, most biopsies are performed under real-time imaging guidance (e.g. ultrasound, mammography or MRI). Biopsies can be performed using vacuum-assisted biopsy devices, which can be better than conventional devices. After the biopsy samples are taken, a tissue marker is placed at the biopsy site utilizing a separate marker placement device. This is followed by mammogram to verify the location of the marker. Marker placement is a very important step and is routinely done. The marker marks the site of biopsy and helps to confirm that the biopsy was actually obtained from the mass or area of calcification or suspicious area, and not from adjacent normal breast tissue. If the pathology comes back benign, and no further treatment is deemed necessary, the marker will mark the area of interest and in future imaging (generally mammogram) the physician will know that the site marked with marker was benign and will not confuse with suspicious abnormality. If the pathology is malignant so that the mass or suspected area has to be surgically removed, the marker will serve as a target for the physician to place localization wire which will guide the surgeon to remove the mass or the area of interest. The marker should be placed at the correct site of the biopsy, and the marker should not be moved or get displaced during or after the deployment.

There are several disadvantages of currently available biopsy devices and marker placement devices. First, two separate devices have to be used. Once biopsy is done, the biopsy cannula or needle is taken out from the breast and a new marker placement needle is percutaneously inserted into the breast the tip aiming at the biopsy site, followed by deployment of the marker. For example, a biopsy apparatus for obtaining tissue samples is disclosed by Miller in U.S. Pat. No. 6,638,235, which is incorporated herein by reference in its entirety. After completion of the biopsy sampling, a separate apparatus like the device described by Chesbrough in U.S. Pat. No. 8,052,708 (or other similar devices) is inserted percutaneously to deploy the tissue marker.

There are several disadvantages with these techniques. First, there is increased procedure time and patient discomfort as the insertion has to be done twice. Double insertion also increases the trauma to the breast tissue. Sometimes it is difficult to insert the marker placement needle to the exact site of biopsy especially in patients with dense breast which tend to have increased resistant to the insertion of the needle. Conversely, large or fatty breasts tend to have low resistance, and the marker can move away from the site of the biopsy.

It is possible to obviate the need of double insertion by either leaving a sheath or the outer cannula of the biopsy apparatus so that a marker placement device can be inserted through the sheath or the outer cannula. For example, a device as described by Selis in U.S. Pat. No. 8,454,629 can be used for such applications. The disadvantage of this technique is that another device is needed and also another step is needed in part of the physician increasing cost and procedure time. The sheath or the outer cannula of the biopsy device left in place to serve the purpose of port for marker placement device tends to move especially with ultrasound guided techniques as the physician has to disconnect the cannula or the sheath from the remaining part of the biopsy system and retract the remaining of the biopsy system.

In addition, with all types of available devices and methods performed under ultrasound guidance, the physician or technologist is required to hold the ultrasound probe in place while getting ready for marker placement. In any case due to dead time and extra steps, the ultrasound probe tends to move from the site. This causes problems in accurate site localization for deployment of the marker as small lesions will be completely removed during biopsy procedure and the physician will have to guess the area of biopsy.

There are systems in which back end of the biopsy system can be opened and the marker placement device is inserted through the inner cannula of the biopsy system. For example, as described by Beckman in U.S. Pat. No. 7,465,279. However such methods have disadvantage of needing two separate devices and also two different people, one for holding the biopsy system and another for inserting the marker placement device. Again during such maneuver, there is the possibility of some movement of the biopsy cannula and marker deployment site may not be accurate. Also this involves extra step in the procedure increasing the procedure time and patient discomfort.

There is an intrinsic mechanical problem of utilizing the main lumen of the outer cannula of the biopsy device as a port of the marker placement device insertion. The outer needle or cannula has lateral opening forming a tissue receiving port. Although the needle is supposed to be rotated 180 degrees after the deployment of the marker through the port to prevent entrapment of the marker into the port and subsequent displacement after deployment or complete retraction with the retraction of the needle, such problems are not completely resolved with rotation technique and the marker can get entrapped in the port and rotate with the needle and subsequently get lodged into an incorrect site or get completely retracted.

Given the abovementioned disadvantages of the currently available biopsy and marker placement methods and devices, further improvements in the methods and devices continue to be of interest. There is a need of a single apparatus to perform both functions. It is in the interest of the patient, physician and our society not only to decrease the cost of procedure but also to decrease the time needed to do the procedure. These can be done utilizing the embodiments disclosed herein, which can eliminate the need of using two different devices. A single device for biopsy sampling and marker placement can potentially decrease the cost of the procedures. This involves fewer steps to be done by the physician, thus decreasing procedure time and improving patient outcome, including patient comfort and satisfaction. This also can decrease health care costs.

SUMMARY

Embodiments of a system, method and apparatus for integrated tissue sampling and tissue marker placement are disclosed. For example, an apparatus can include integrated tissue sampling and marker placement systems that can decrease the procedure time and potentially decrease the equipment cost. This can improve the positional accuracy of the marker placement and can help prevent marker displacement after deployment, which can lead to overall patient and physician satisfaction. In some embodiments, methods of biopsy and tissue marker placement are disclosed. These can provide an integrated, dual-function, disposable apparatus for obtaining tissue samples and placing tissue marker using a single device and single insertion.

The foregoing and other objects and advantages of these embodiments will be apparent to those of ordinary skill in the art in view of the following detailed description, taken in conjunction with the appended claims and the accompanying drawings.

BRIEF DESCRIPTION OF THE DRAWINGS

So that the manner in which the features and advantages of the embodiments are attained and can be understood in more detail, a more particular description may be had by reference to the embodiments thereof that are illustrated in the appended drawings. However, the drawings illustrate only some embodiments and therefore are not to be considered limiting in scope as there may be other equally effective embodiments.

FIG. 1 is a schematic, partially sectioned top view of an embodiment of a biopsy device and integrated marker placement system.

FIG. 2 is a schematic, sectional end view of an embodiment of the system of FIG. 1, taken along the line 2-2 of FIG. 1.

FIG. 3 is another schematic, sectional end view of an embodiment of the system of FIG. 1, taken along the line 3-3 of FIG. 1.

FIG. 4 is a schematic, partially sectioned top view of another embodiment of a biopsy device and integrated marker placement system.

FIG. 5 is a schematic, sectional end view of an embodiment of the system of FIG. 4, taken along the line 5-5 of FIG. 4.

FIG. 6 is another schematic, sectional end view of an embodiment of the system of FIG. 4, taken along the line 6-6 of FIG. 4.

The use of the same reference symbols in different drawings indicates similar or identical items.

DETAILED DESCRIPTION

Figure 7:
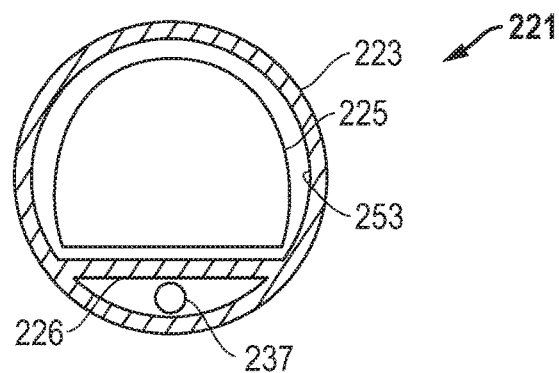
FIG. 7 is a schematic, sectional end view of an alternate embodiment of a system.

Embodiments of a system, method and apparatus for a biopsy or tissue sampling with an integrated tissue marker placement are disclosed. For example, FIGS. 1-3 depict a device 21 that can include an axis 22, an outer cannula 23 having a primary lumen 53 and an inner cannula 25 having an inner lumen 26. The outer and inner cannulas 23, 25 can be mounted to a hand piece or actuator 27. In some examples, the actuator 27 can house a system for actuation and/or vacuum production, such as one of an ATEC, Celero or Sertera breast biopsy systems, from Hologic, Inc., located in Marlborough, Mass. Any of these devices, or others, can be modified in accordance with the embodiments described herein, such as to actuate a marker deployment device.

At its proximal end, the inner cannula 25 can be connected to a tissue collection system 29, which is illustrated schematically, in dashed line, smaller than its actual size. The outer cannula 23 can have a tissue receiving port 31 along one lateral side, and a marker deployment aperture 33 that can be opposite the tissue receiving port 31, in some versions. The distal end of the outer cannula 23 can have a cutting edge 35 for penetration into tissue. In an example, the marker deployment aperture 33 can be positioned along the axial length of the device 21 at a mid-line 32 (FIG. 1) of the tissue receiving port 31 or distal thereto, as indicated by arrows 34. In other examples, the marker deployment aperture 33 can be placed in different positions.

In some versions, the inner cannula 25 can consist of a single, continuous (monolithic) tube extending from adjacent the tissue receiving port 31 to the tissue collection system 29, as shown. In other versions, the inner cannula 25 can comprise two or more tubular bodies (e.g., tubes) that are in fluid connection with each other. In an example, the outer surface of the inner cannula 25 can be textured within the actuator 27 for better grip and manipulation by the motor system in the actuator 27. The texture on the exterior of inner cannula 25 can assist with both axial motion and rotational motion. Embodiments of the texture can include knurling or other textures known to those of ordinary skill in the art.

In some embodiments, a secondary lumen 41 can extend through the outer cannula 23. The secondary lumen 41 can be radially external to the inner cannula 25. The secondary lumen 41 can be inside, within the body of or outside of the outer cannula 23. A marker 37, such as a biopsy marker, can be positioned within the secondary lumen 41 near a marker deployment aperture 33, such as adjacent to the cutting edge 35. In some examples, the marker 37 can comprise a Securmark or TriMark breast biopsy marker, from Hologic, Inc., located in Marlborough, Mass. The marker 37 can include one or more markers, such as a train of markers that can be individually deployed.

Embodiments of the marker 37 can be adjacent to the distal end of a secondary lumen 41. The secondary lumen 41 also can be positioned within an annulus between the outer and inner cannulas 23, 25. The annulus can be defined as the thin space between the outer and inner cannulas 23, 25 where the secondary lumen 41 can be placed. In some versions, there is fluid connection between the annulus and inner lumen 26 of the inner cannula 25. In other versions, there is no fluid connection between the primary lumen 53 and the secondary lumen 41. The secondary lumen 41 can be outside the inner wall of the outer cannula 23.

The marker deployment aperture 33 of the outer cannula 23 can be located at the distal end of the secondary lumen 41, such as within the outer cannula 23. Relative to axis 22, the marker deployment aperture 33 and the tissue receiving port 31 can be opposite to each other (i.e., aligned 180 degrees apart about axis 22). An axial movement device, such as a plunger 43, can be positioned in the secondary lumen 41 and configured to deploy the marker 37. The plunger 43 can enter the secondary lumen 41 via a proximal opening 45 in the body of the outer cannula 23. A button 51, such as an actuation button, can be provided for the plunger 43 on the actuator 27.

The embodiments of FIGS. 2 and 3 depict a teardrop shape (in radial cross-section, relative to axis 22) for the outer cannula 23. Such a design can include the primary lumen 53 inside the outer cannula 23, and the secondary lumen 41 for deployment of the marker 37. The axially-sectional, outer shape of the primary lumen 53 can be circular to be complementary to the inner cannula 25, whereas the secondary lumen 41 can be present in a radially thicker portion 42 of the outer cannula 23, as opposed a radially thinner portion 44 of the outer cannula 23. The inner surface shape of the secondary lumen 41 also can be also circular to be complementary to the outer shape of the plunger 43. Other shapes that are complementary to the outer shape of the plunger 43 also can be employed.

In an embodiment of a method of using the system, biopsy samples can be obtained using conventional techniques that use the outer and inner cannulas 23, 25 mounted to the actuator 27. For example, the inner cannula 25 can be axially moved (see large arrows in FIG. 1) relative to the outer cannula 23 to obtain one or more biopsy samples through tissue port 31 via vacuum system 61 (FIG. 1), which can be coupled to inner cannula 25 and include a collection trap for the biopsy samples. The device 21 can include a rotary motor as well as an axially reciprocating motor, and the device 21 can be hydraulically, pneumatically, magnetically and/or electrically actuated, in some examples.

Once the biopsy sampling is completed, the plunger 43 can be actuated via the button 51 on the actuator 27 so the marker 37 can be deployed via the marker deployment aperture 33 of the secondary lumen 41. The outer cannula 23 can then be removed from the tissue to complete both the biopsy sampling and the tissue marker placement with a single device and single insertion in the tissue.

FIGS. 4-6 depict an alternate embodiment of a device 121 having an axis 122, an outer or primary cannula 123, an inner or secondary cannula 125, actuator 127, biopsy collection aperture 131, marker deployment aperture 133 and cutter 135. In addition, the device 121 can include a deployment fixture 157 having a secondary lumen 141 provided on an exterior of the outer cannula 123. The deployment fixture 157 can have the marker deployment aperture 137 and be used to deploy the marker 137 with the plunger 143. A hub 124 of the device 121 and the deployment fixture 157 can both include openings 145 for the plunger 143 to extend through. In the illustrated example, the plunger 143 can extend from an interior of actuator 127 and hub 124, to an exterior of the device 121, and then into the secondary lumen 141 in the deployment fixture 157. For such embodiments, the plunger 143 can be appropriately sealed to maintain the independence of its operation and actuation from that of the tissue sampling device.

Figure 11:
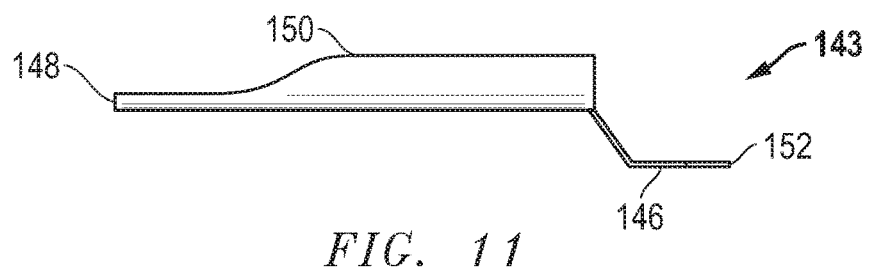
FIGS. 11-13 are schematic side, top and end views of an embodiment of a plunger.
Figure 12:
Figure 13:
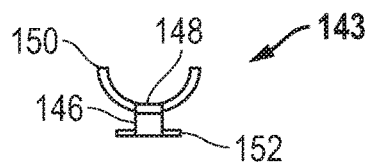

Alternatively, the plunger 143 can include an external portion 146 that does not extend through hub 124, but is located entirely on an exterior of the hub 124 and actuator 127. One example of the plunger 143 is depicted in FIGS. 11-13. In this version, the plunger 143 comprises a partial sheath plunger, and can include a tip 148 for engaging the marker, a body 150 that is complementary in shape to an exterior of the device 121, and an actuation handle 152 adjacent the external portion 146. In another example, a proximal portion of the plunger 143 can be located inside the actuator 127, and the actuator 127 can include a switch or button (see, e.g., button 51 in FIG. 1) to actuate the plunger 143.

In addition, the primary cannula 123 can include a hub 124 for connection to the actuator 127. Versions of the hub 124 can be formed with the primary cannula 123 such that they are connected or even form a continuous, monolithic component. In some embodiments, the hub 124 can help facilitate vacuum-assistance for the device 121. For example, the hub 124 can facilitate fluid to be provided to the primary lumen 153 of the outer cannula 123. Examples of the fluid can include one or more of air, liquid irrigation (e.g., saline) or local anesthetic.

In some embodiments, the primary cannula 123 can have a variable axial shape along axis 122. For example, a proximal portion (along section line 5-5 of FIG. 4) of the primary cannula 123 can be circular (FIG. 5) in radial sectional shape between the hub 124 and the distal portion of the primary cannula 123. In contrast, the distal portion (along section line 6-6 of FIG. 4) of the primary cannula 123 can have a non-circular shape (e.g., teardrop shape), as shown in FIG. 6. Other shapes that can incorporate the marker and its deployment also can be used, such as those that would enable the marker to be deployed opposite the biopsy collection, as described herein. During the medical procedure, such shaped configurations of the primary cannula 123 can vertically align with the linear, vertical incision made in a patient, which can improve patient comfort during the procedure.

Thus, the exterior of the primary cannula 123 can be complemented in shape by at least a partial sheath (see plunger 143 in FIGS. 4-6) on an exterior of primary cannula 123. The partial sheath can be narrow, such as pointed, toward the distal end, which can be used to deploy the marker 137 from the marker deployment aperture 133. The marker 137 can be deployed independently from the biopsy collection process of the device 121.

FIG. 7 depicts another embodiment of a device 221 having an outer cannula 223 and an inner cannula 225. In this version, outer cannula 223 can be circular in shape (as shown), but segmented by an inner panel or wall 226. Wall 226 can be used to independently seal and separate the marker 237 and the marker deployment function from the remaining interior 253 and biopsy collection of the device 221. Thus, each of the marker deployment function and the biopsy collection function can be independently actuated or performed without affecting the other function. In addition, the inner cannula 225 can be provided with a D-shaped sectional end view profile. Such profiles can be configured to deter relative rotation between outer cannula 223 and inner cannula 225, which can be desirable for some applications.

Figure 14:
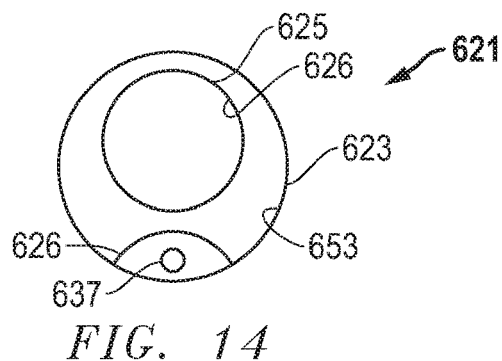
FIGS. 14 and 15 are schematic, axial end views of additional embodiments of integrated tissue sampling and marking devices.
Figure 15:
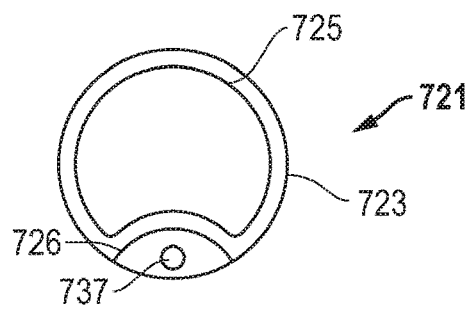

Other alternate embodiments of a device 621 (FIG. 14) can include an outer cannula 623 with a circular radial profile and a primary lumen 653. An inner cannula 625 having a circular radial profile and an inner lumen 626 can be located inside the outer cannula 623. The device 621 can further include a partition or wall 626 located inside and extending the entire axial length of outer cannula 623. Walls 626 can separate marker 637 and the marker deployment function from the annulus between the interior of the outer cannula 623 and the exterior of the inner cannula 625. The annulus can have a variable radial thickness or profile, as shown. In another version (FIG. 15), the inner cannula 725 of the device 721 can be contoured to be complementary in shape to the wall 726 inside the outer cannula 723 that separates the marker 737. In the version shown, the inner cannula can be moon-shaped, kidney-shaped, etc., in radial sectional profile, having both convex and concaves shapes.

Figure 8:
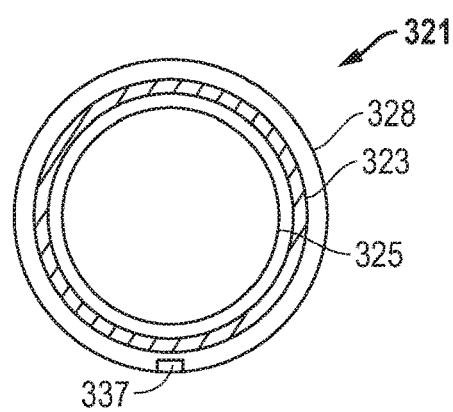
FIG. 8 is a schematic, sectional end view of yet another embodiment of a system.

FIG. 8 depicts an embodiment of still another system 321 having an outer cannula 323 and an inner cannula 325. In this version, the exterior of the outer cannula 323 can be circular and located completely inside a sheath 328. Examples of the outer cannula 323 can be both axially and rotationally movable within the sheath 328. The space between the interior of the sheath 328 and the exterior of the outer cannula 323 can provide a pathway, such as through as a secondary lumen, to provide a marker deployment system for a marker 337. The marker 337 can be deployed independently from the biopsy collection process of system 321. Such embodiments can be implemented and can be equivalent to using the annulus (described above) as the secondary lumen. These embodiments can comprise non-circular shapes, such as a teardrop shape, a D-shape and/or other adherent shapes as well. In some versions, the sheath does not need to move or rotate, so its outer non-circular shape does not cause any issues and the teardrop shape can be beneficial.

Figure 10:
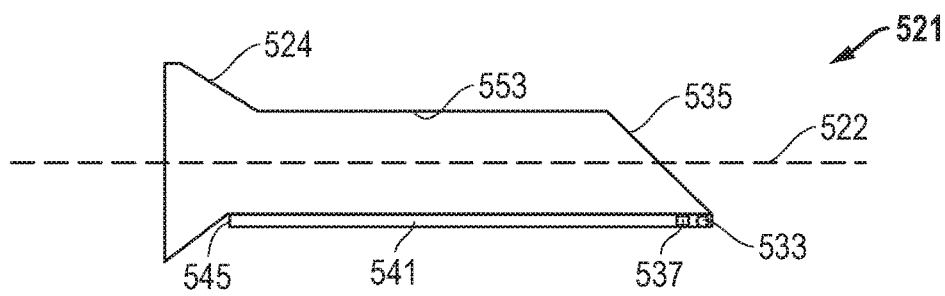
FIG. 10 is a schematic, partially sectioned top view of an embodiment of an introducer device.

The embodiment of FIG. 8 can be used in conjunction with one or more of the features shown and described elsewhere herein. In other examples, embodiments of the marker can be integrated into an introducer 521 (FIG. 10) comprising a hollow tube with an axis 522 that is open on each axial end, at both its hub 524 and its cutting edge 535. The introducer 521 can be co-axial with the other components or their axes can be eccentric to each other. The primary lumen 553 of the co-axial introducer 521 can be a port for a biopsy needle, and a secondary lumen 541 having an entry port 545 and a marker deployment aperture 533 can be provided for the marker 537 and a plunger or other marker deployment device.

As noted herein, the sheath 328 can completely circumscribe the outer cannula 323. The sheath embodiments can be more suitable for stereotactic and/or magnetic resonance imaging (MRI) procedures for integrated biopsy collection and marker deployment systems that are actuated independently of each other by a single device. Alternatively, the marker can be directly attached adjacent to or at a distal end of the sheath 328 itself for deployment therefrom after one or more biopsy samples is taken by a biopsy collection tool used within the sheath 328.

Figure 9:
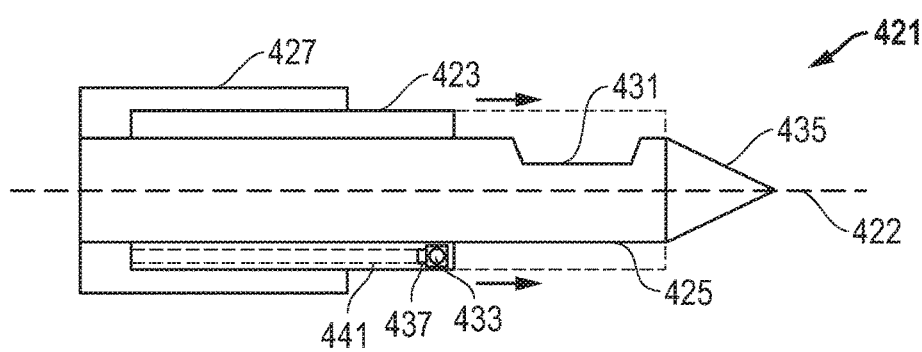
FIG. 9 is a schematic, partially sectioned top view of still another embodiment of a biopsy device and integrated marker placement system.

In the embodiment of FIG. 9, the device 421 can include an inner cannula 425 (which, alternatively, can be a solid stylet) that is stationary or axially moveable, and an axially movable (relative to axis 422) outer cannula 423. The inner cannula 423 can comprise the tissue receiving port 431, in this version, for collecting one or more biopsy samples when the outer cannula 423 is actuated (see large arrows) to the dashed line position shown in FIG. 9 adjacent cutting edge 435 on the inner cannula 425. This design can be a self-contained unit with actuator 427, can be spring-actuated, and can include no form of vacuum assistance. The device 421 also can deploy a marker 437 via the marker deployment aperture 433 in the outer cannula 423. The device 421 may or may not include a secondary lumen 441. In some versions, the embodiment may not include a lumen of the inner cannula 425 when it is a solid stylet.

The embodiments disclosed herein can fulfill the need for a dual-function, biopsy and marker placement apparatus by providing a single, integrated device in which the marker deployment function is independently contained and actuated within a single apparatus in such a way that the aforementioned limitations of conventional solutions and methods are overcome. The device can be hand held or fixed to a support fixture.

Embodiments of the device can be disposable, and can include the outer cannula with the cutting tip at the distal end, and the inner cannula with a sharp cutting edge. The cannulas can be mounted to an actuator. The outer cannula can include two lumens, including a primary lumen for the inner cannula, and a secondary lumen for the marker and marker deployment plunger. The outer cannula can include a tissue receiving port where biopsied tissue can be moved and placed with a vacuum system. The tissue can be severed with the axial or axial and rotational movement of the inner cannula, which has a lumen to transport the tissue back to the collection system. Examples of vacuum-assisted breast biopsy systems were previously provided.

Opposite the tissue receiving port on the other side of the outer cannula there can be an aperture for deployment of the tissue marker. The marker aperture can be at the distal end of the secondary lumen of the outer cannula. The outer cannula can be made in such a way that it has an inner circular lumen where the inner cannula slides back and forth to obtain the tissue samples. The inner cannula and primary lumen can be independent of and operate/function independently of the secondary lumen.

The shape of the outer cannula can be generally non-uniform in shape in an end sectional view. In some versions, the apical aspect of the shape can include the secondary lumen. A plunger can be placed inside of the secondary lumen and the actuation button for the plunger can be positioned on the actuator or hand piece. A tissue marker can be placed at the distal end of the secondary lumen. The marker can be deployed by using the plunger. Once the biopsy is performed, the plunger can be actuated to deploy the marker. Once the marker is deployed the entire system can be removed from the tissue. Such designs can prevent the entrapment of the marker in the receiver port as the marker is deployed from the opposite side. This can allow the physician to place the tissue marker at the exact location of the biopsy. As the aperture for marker deployment is at opposite side but at almost the same longitudinal depth of the biopsy tissue receiving port, the marker can lodge in the resection cavity that remains in the tissue after removal of the biopsy sample.

The entire procedure can be done with a single insertion, and a single device, thereby increasing the accuracy of the procedure, decreasing the total time required for the procedure and, thus, improving patient satisfaction and comfort while decreasing the time and potential cost of the procedure. Examples of this system can be used with ultrasound, mammography and MRI guided procedures.

One advantage of the non-circular shaped embodiments of the outer cannula is that these shapes can be less traumatic to the tissue at initial insertion, as this corresponds with the slit incision made to insert the biopsy needle. Such shapes can have less tissue resistance during initial insertion through the skin incision compared to a circular shape for the outer cannula. However, making the proximal portion of the system more circular (see FIGS. 4 and 5) can prevent tissue resistance during the rotation of the needle while obtaining multiple samples.

In another embodiment, the outer cannula with secondary lumen can include a marker placement needle adherent to the outer cannula opposite to the tissue reception port. In yet another embodiment, the plunger system can include a safety feature that is required to be released prior to deployment of the marker to prevent accidental marker deployment. In still another embodiment, the marker aperture can be placed at the distal end of the outer cannula. In such versions, the marker may not be at the same level of the center of the biopsy cavity and the physician may have to retract the cannula prior to deployment of the marker to make sure the marker falls at the center of the biopsy site.

Other versions may include one or more of the following embodiments:

1. A medical device, comprising:
   an actuator configured to be manipulated by an operator of the medical device;
   an outer cannula extending from the actuator along an axis, and the outer cannula comprises a primary lumen extending through the outer cannula to a tissue reception port formed in the outer cannula;
   an inner cannula located inside the outer cannula and extending in an axial direction, the inner cannula having an inner lumen extending through the inner cannula that is configured to be actuated to collect a tissue sample via the tissue reception port and transport the tissue sample;
   a marker placement device located in or adjacent to the primary lumen of the outer cannula, wherein the marker placement device is configured to be actuated to deploy a marker at a biopsy site via a marker deployment port; and
   tissue sampling and marker placement functions are integrated within the medical device such that the medical device consists of a single apparatus configured to perform both tissue sampling and marker placement functions, and the marker placement function is independent of and separately operable from the tissue sampling function.

2. The medical device of any of these embodiments, wherein the inner cannula is co-axial with the outer cannula.

3. The medical device of any of these embodiments, wherein the tissue reception port and the marker deployment port are located on opposite radial sides of the outer cannula, relative to the axis.

4. The medical device of any of these embodiments, wherein the secondary lumen is located inside the primary lumen of the outer cannula, the secondary lumen is physically separated from the primary lumen by a partition, the marker deployment port extends from the primary lumen to an exterior of the outer cannula, and a distal end of the secondary lumen is adjacent the marker deployment port.

5. The medical device of any of these embodiments, wherein the secondary lumen is external to the outer cannula and adjacent to an exterior surface of the outer cannula, and the secondary lumen comprises the marker deployment port.

6. The medical device of any of these embodiments, further comprising a tissue collection system coupled to a proximal end of the inner cannula.

7. The medical device of any of these embodiments, wherein the tissue collection system comprises a vacuum system, and the vacuum system is either internal to the actuator or external of the actuator.

8. The medical device of any of these embodiments, wherein the tissue collection system does not comprises a vacuum system.

9. The medical device of any of these embodiments, wherein the actuator comprises a deployment switch for actuating a plunger inside the secondary lumen to deploy the marker through the marker deployment port.

10. The medical device of any of these embodiments, wherein the marker is retained in a retained position prior to actuation of the plunger.

11. The medical device of any of these embodiments, wherein the plunger retains the marker in a retained position prior to actuation of the plunger.

12. The medical device of any of these embodiments, wherein the outer cannula has a radial sectional shape taken perpendicular to the axis, the radial sectional shape comprises a teardrop shape, and the marker placement device is located in an annulus between the primary lumen and an exterior of the inner cannula.

13. The medical device of any of these embodiments, wherein the outer cannula has a radial sectional shape taken perpendicular to the axis, the radial sectional shape comprises a circular shape, and the marker deployment device is located outside and attached to an exterior of the outer cannula.

14. The medical device of any of these embodiments, wherein the actuator is one of automated or manually gripped and actuated by the operator of the medical device.

15. The medical device of any of these embodiments, wherein the tissue sampling function is sealed and isolated from the marker placement function.

16. The medical device of any of these embodiments, wherein the tissue sampling function and the marker placement function are actuated by separate and independent components of the medical device.

17. The medical device of any of these embodiments, wherein the medical device does not comprise a sheath that is external to the outer cannula.

18. The medical device of any of these embodiments, where a vacuum is applied to the primary lumen via the inner lumen during the tissue sampling, the vacuum is terminated before actuation of the marker deployment device, and no portion of the medical tool is required to be rotated during operation.

19. The medical device of any of these embodiments, wherein the marker is configured to locate in a void formed by removal of a tissue sample.

20. A medical device, comprising:
   an actuator configured to be manipulated by an operator of the medical device;
   an outer cannula extending from the actuator, the outer cannula having a tissue sampling lumen configured to take a tissue sample, and a marker placement lumen configured to deploy a marker, the tissue sampling lumen of the outer cannula contains one of an inner cannula, a stylet or a tissue receiving system, the marker placement lumen contains a plunger configured to deploy the marker, wherein both the tissue sampling and marker deployment are integrated into the medical device, the medical device consists of only one apparatus, the tissue sampling and marker deployment are mechanically compartmentalized and functionally separated from each other within the only one apparatus, and are not in fluid communication with each other such that the tissue sampling and marker deployment function independently of each other.

21. A medical device, comprising:
an actuator configured to be manipulated by an operator of the medical device;
an outer cannula extending from the actuator along an axis, and the outer cannula comprises a hub mounted to the actuator, and a primary lumen extending through the outer cannula to a tissue reception port formed in the outer cannula, and the outer cannula comprises a variable axial shape along the axis, the variable axial shape comprises a proximal portion that is circular in radial sectional shape between the hub and a distal portion of the primary cannula, and the distal portion is a non-circular in radial sectional shape;
an inner cannula located inside the outer cannula and extending in an axial direction, the inner cannula having an inner lumen extending through the inner cannula that is configured to be actuated to collect a tissue sample via the tissue reception port and transport the tissue sample;
a marker placement device located adjacent to the primary lumen of the outer cannula, wherein the marker placement device is configured to be actuated to deploy a marker at a biopsy site via a marker deployment port; and
tissue sampling and marker placement functions are integrated within the medical device such that the medical device consists of a single apparatus configured to perform both tissue sampling and marker placement functions, and the marker placement function is independent of and separately operable from the tissue sampling function.

22. The medical device of any of these embodiments, wherein the distal portion of the primary cannula comprises a teardrop shape in radial section.

23. The medical device of any of these embodiments, further comprising a partial sheath plunger that is configured to be actuated to deploy the marker, the partial sheath plunger extends axially from adjacent to the hub to adjacent to the marker deployment port.

24. The medical device of any of these embodiments, wherein the partial sheath plunger comprises a variable axial shape and the partial sheath plunger only partially circumscribes the medical device.

25. The medical device of any of these embodiments, wherein the partial sheath plunger is located partially inside the medical device and partially outside of the medical device.

26. A medical device, comprising:
a tissue sampling device comprising:
an actuator configured to be manipulated by an operator of the medical device;
an outer cannula extending from the actuator along an axis, and the outer cannula comprises a primary lumen extending through the outer cannula to a tissue reception port formed in the outer cannula;
an inner cannula located inside the outer cannula and extending in an axial direction, the inner cannula having an inner lumen extending through the inner cannula that is configured to be actuated to collect a tissue sample via the tissue reception port and transport the tissue sample; and the medical device further comprises:
a tube inside which the tissue sampling device is configured to extend, the tube comprises a distal end and a marker placement device located adjacent to the distal end of the tube, wherein the marker placement device is configured to be actuated to deploy a marker at a biopsy site via a marker deployment port in the tube; and tissue sampling and marker placement functions are integrated within the medical device such that the medical device is configured to perform both tissue sampling and marker placement functions, and the marker placement function is independent of and separately operable from the tissue sampling function.

27. The medical device of any of these embodiments, wherein the marker placement device comprises a secondary lumen that extends axially through the tube, and the marker is located inside the secondary lumen adjacent to the marker deployment port which is also in the secondary lumen.

28. The medical device of any of these embodiments, wherein the tissue sampling device comprises a cutting edge, and the tube comprises a sheath without a cutting edge.

29. The medical device of any of these embodiments, wherein the tissue sampling device does not comprise a cutting edge, and the tube comprises an introducer with a cutting edge.

30. The medical device of any of these embodiments, wherein the tube comprises a variable axial shape along the axis, the variable axial shape comprises a proximal portion that is circular in radial sectional shape, and a distal portion that is a non-circular in radial sectional shape.

31. A medical device, comprising:
an actuator configured to be manipulated by an operator of the medical device;
an outer cannula extending from the actuator along an axis, and the outer cannula comprises a primary lumen extending through the outer cannula to a tissue reception port formed in the outer cannula;
an inner cannula located inside the outer cannula and extending in an axial direction, the inner cannula having an inner lumen extending through the inner cannula that is configured to be actuated to collect a tissue sample via the tissue reception port and transport the tissue sample;
a marker placement device located in or adjacent to the primary lumen of the outer cannula, wherein the marker placement device is configured to be actuated to deploy a marker at a biopsy site via a marker deployment port; and
tissue sampling and marker placement functions are integrated within the medical device such that the medical device consists of a single apparatus configured to perform both tissue sampling and marker placement functions, and the marker placement function is independent of and separately operable from the tissue sampling function.

32. The medical device of any of these embodiments, wherein the outer cannula comprises a cutting end, and the tissue reception port and the marker deployment port are located on opposite radial sides of the outer cannula, relative to the axis, adjacent to the cutting end.

33. The medical device of any of any of these embodiments, wherein the secondary lumen is located inside the primary lumen of the outer cannula, the secondary lumen is physically separated from the primary lumen by a partition, the marker deployment port extends from the primary lumen to an exterior of the outer cannula, and a distal end of the secondary lumen is adjacent to the marker deployment port.

34. The medical device of any of any of these embodiments, further comprising a tissue collection system coupled to a proximal end of the inner cannula, and the tissue collection system comprises a vacuum system, and the vacuum system is either internal to the actuator or external of the actuator.

35. The medical device of any of any of these embodiments, wherein the actuator comprises a deployment switch for actuating a plunger inside the secondary lumen to deploy the marker through the marker deployment port.

36. The medical device of any of any of these embodiments, wherein the outer cannula has two different radial sectional shapes taken perpendicular to the axis, a first one of the radial sectional shapes comprises a non-circular shape, and a second one of the radial sectional shapes comprises a circular shape.

37. The medical device of any of any of these embodiments, wherein the tissue sampling function is sealed and isolated from the marker placement function, and the tissue sampling function and the marker placement function are actuated by separate and independent components of the medical device.

38. The medical device of any of any of these embodiments, wherein the medical device does not comprise a sheath that is external to the outer cannula.

39. The medical device of any of any of these embodiments, wherein the outer cannula comprises a hub mounted to the actuator, and the outer cannula comprises a variable axial shape along the axis, the variable axial shape comprises a proximal portion that is circular in radial sectional shape between the hub and a distal portion of the outer cannula, and the distal portion is a non-circular in radial sectional shape.

40. The medical device of any of any of these embodiments, wherein a distal portion of the outer cannula comprises a teardrop shape in radial section.

41. The medical device of any one of any of these embodiments, further comprising a partial sheath plunger that is configured to be actuated to deploy the marker, the partial sheath plunger extends axially from adjacent to the actuator to adjacent to the marker deployment port.

42. The medical device of any one of any of these embodiments, further comprising a partial sheath plunger having a variable axial shape, and the partial sheath plunger only partially circumscribes the medical device.

43. The medical device of any one of any of these embodiments, further comprising a partial sheath plunger located partially inside the medical device and partially outside of the medical device.

44. The medical device of any of any of these embodiments, wherein the outer cannula comprises a tube having a distal end and the marker is located adjacent to the distal end of the tube, wherein the marker is configured to be deployed by a plunger in the tube at a biopsy site via the marker deployment port in the tube.

45. A medical device, comprising:
an actuator configured to be manipulated by an operator of the medical device;
an outer cannula extending from the actuator along an axis, and the outer cannula comprises a primary lumen extending through the outer cannula;
an inner cannula located inside the outer cannula and extending in an axial direction, the inner cannula comprises a solid component without an inner lumen extending through the inner cannula;
a marker placement device located in or adjacent to the primary lumen of the outer cannula, wherein the marker placement device is configured to be actuated to deploy a marker at a biopsy site via a marker deployment port; and
a tissue reception port configured to be actuated to collect a tissue sample.

This written description uses examples to disclose the embodiments, including the best mode, and also to enable those of ordinary skill in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

It may be advantageous to set forth definitions of certain words and phrases used throughout this patent document. The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A medical device, comprising:
    an actuator configured to be manipulated by an operator of the medical device;
    an outer cannula extending from the actuator along an axis, and the outer cannula comprises a closed distal end with a cutting edge, a primary lumen extending through the outer cannula to a tissue reception port formed in and extending through a radial wall of the outer cannula relative to the axis and the tissue reception port is located proximal to the cutting edge;
    an inner cannula located inside the outer cannula and extending in an axial direction, the inner cannula having an inner lumen extending through the inner cannula that is configured to be actuated toward a back of the cutting edge to collect a tissue sample via the tissue reception port and transport the tissue sample coaxial with the primary lumen and the inner lumen;
    a marker placement device having a secondary lumen separated from the primary lumen of the outer cannula by a wall, wherein the marker placement device is configured to be actuated to deploy a marker external to the medical device at a biopsy site via a marker deployment port that is proximal to the cutting edge, and the tissue reception port and the marker deployment port are located on opposite radial sides of the outer cannula, relative to the axis; and
    wherein tissue sampling and marker placement functions are integrated within the medical device such that the medical device operates as a single apparatus configured to perform both tissue sampling and marker placement functions, and wherein the wall separating the primary lumen from the secondary lumen serves to independently seal and separate the marker placement function from the tissue sampling function.

2. The medical device of claim 1, wherein the inner cannula is co-axial with the outer cannula.

3. The medical device of claim 1, wherein the marker deployment port is positioned in proximity to the a distal end of the secondary lumen.

4. The medical device of claim 1, wherein the secondary lumen is axially aligned with the primary lumen of the outer cannula.

5. The medical device of claim 4, wherein the marker placement device comprises a plunger, and the actuator comprises a deployment switch for actuating the plunger inside the secondary lumen to deploy the marker through the marker deployment port.

6. The medical device of claim 5, wherein the marker is retained in a retained position prior to actuation of the plunger.

7. The medical device of claim 5, wherein the plunger retains the marker in a retained position prior to actuation of the plunger.

8. The medical device of claim 1, further comprising a tissue collection system coupled to a proximal end of the inner cannula.

9. The medical device of claim 8, wherein the tissue collection system comprises a vacuum system that evacuates the tissue sample coaxial with the primary lumen and the inner lumen, and the vacuum system is either internal to the actuator or external of the actuator.

10. The medical device of claim 8, wherein the tissue collection system does not comprises a vacuum system.

11. The medical device of claim 1, wherein the outer cannula has a radial sectional shape taken perpendicular to the axis, the radial sectional shape comprises a teardrop shape, and the marker placement device is located in an annulus between the primary lumen and an exterior of the inner cannula.

12. The medical device of claim 1, wherein the outer cannula has a radial sectional shape taken perpendicular to the axis, the radial sectional shape comprises a circular shape, and the marker placement device is located outside and attached to an exterior of the outer cannula.

13. The medical device of claim 1, wherein the actuator is one of automated or manually gripped and actuated by the operator of the medical device.

14. The medical device of claim 1, wherein the tissue sampling function is sealed and isolated from the marker placement function.

15. The medical device of claim 1, wherein the tissue sampling function and the marker placement function are actuated by separate and independent components of the medical device.

16. The medical device of claim 1, wherein the medical device does not comprise a sheath that is external to the outer cannula.

17. The medical device of claim 1, where a vacuum is applied to the primary lumen via the inner lumen during the tissue sampling, the vacuum is terminated before actuation of the marker placement device, and no portion of the medical tool is required to be rotated during operation.

18. A medical device, comprising:
    an actuator configured to be manipulated by an operator of the medical device;
    an outer cannula extending from the actuator, the outer cannula having a tissue sampling lumen configured to take a tissue sample, and a marker placement lumen configured to deploy a marker, the tissue sampling lumen of the outer cannula contains one of an inner cannula, a stylet or a tissue collection system, the marker placement lumen separated from the tissue sampling lumen by a wall and containing a plunger configured to deploy the marker, wherein both the tissue sampling function and marker deployment function are integrated into the medical device, such that the medical device operates as a single apparatus configured to perform both the tissue sampling and marker placement functions, and wherein the wall separating the tissue sampling lumen from the marker deployment lumen serves to mechanically compartmentalize and functionally separate the tissue sampling function from the marker deployment function.

19. A medical device, comprising:
    an actuator configured to be manipulated by an operator of the medical device;
    an outer cannula extending from the actuator along an axis, and the outer cannula comprises a hub mounted to the actuator, and a primary lumen extending through the outer cannula to a tissue reception port formed in the outer cannula, and the outer cannula comprises a variable axial shape along the axis, the variable axial shape comprises a proximal portion that is circular in radial sectional shape between the hub and a distal portion of the outer cannula, and the distal portion is non-circular in radial sectional shape;

an inner cannula located inside the outer cannula and extending in an axial direction, the inner cannula having an inner lumen extending through the inner cannula that is configured to be actuated to collect a tissue sample via the tissue reception port and transport the tissue sample;

a marker placement device having a secondary lumen separated from the primary lumen of the outer cannula by a wall, wherein the marker placement device is configured to be actuated to deploy a marker at a biopsy site via a marker deployment port; and wherein the tissue sampling and marker placement functions are integrated within the medical device such that the medical device operates as a single apparatus configured to perform both tissue sampling and marker placement functions, and wherein the wall separating the primary lumen from the secondary lumen serves to independently seal and separate the marker placement function from the tissue sampling function.

* * * * *